US010206021B2

(12) United States Patent
Lahti et al.

(10) Patent No.: US 10,206,021 B2
(45) Date of Patent: Feb. 12, 2019

(54) GAS DETECTOR FOR MOBILE DEVICE INCLUDING ENCLOSURE HAVING INTERIOR CHAMBER WITH AUDIO LOUDSPEAKER, SEALED LOUDSPEAKER OPENING, VENTILATION PORT, AND GAS SENSOR

(71) Applicant: Intel Corporation, Santa Clara, CA (US)

(72) Inventors: Saku Lahti, Tampere (FI); Mikko S. Komulainen, Tampere (FI); Tapio Liusvaara, Tampere (FI)

(73) Assignee: INTEL CORPORATION, Santa Clara, CA (US)

( * ) Notice: Subject to any disclaimer, the term of this patent is extended or adjusted under 35 U.S.C. 154(b) by 95 days.

(21) Appl. No.: 14/977,836

(22) Filed: Dec. 22, 2015

(65) Prior Publication Data
US 2017/0176330 A1   Jun. 22, 2017

(51) Int. Cl.
| H04R 1/02 | (2006.01) |
| G01N 27/00 | (2006.01) |
| H04R 1/28 | (2006.01) |
| G01N 33/00 | (2006.01) |

(Continued)

(52) U.S. Cl.
CPC ............ *H04R 1/028* (2013.01); *G01N 27/00* (2013.01); *G01N 33/00* (2013.01); *H04R 1/2826* (2013.01); *G01N 21/3504* (2013.01); *H04R 29/003* (2013.01); *H04R 2400/00* (2013.01); *H04R 2499/11* (2013.01)

(58) Field of Classification Search
CPC ........ G01N 21/61; G01N 33/00; G01N 27/00; G01N 21/3504; H04R 1/028; H04R 1/2826; H04R 2499/11; H04R 2400/00; H04R 29/003
See application file for complete search history.

(56) References Cited

U.S. PATENT DOCUMENTS

| 2005/0085275 A1* | 4/2005 | Hugunin ............... H04M 19/04 |
| | | 455/567 |
| 2008/0025542 A1* | 1/2008 | Lee ....................... H04M 1/035 |
| | | 381/334 |

(Continued)

OTHER PUBLICATIONS

Marshall Leach, Vented-Box Loudspeaker Design with a Given Driver, 2001, Kendall/Hunt, p. 1.*

*Primary Examiner* — Michael P LaPage
(74) *Attorney, Agent, or Firm* — Finch & Maloney PLLC (57) ABSTRACT

A gas detection device includes an enclosure having an interior chamber, an audio loudspeaker in acoustic communication with the interior chamber of the enclosure, and a gas sensor configured to detect a gas within the interior chamber of the enclosure. The device may include a ventilation port configured to permit two-way gaseous communication between the interior chamber and an atmosphere external to the enclosure, where the atmosphere comprises the gas. The audio loudspeaker is configured to generate a pressure within the interior chamber. The pressure causes a portion of the external atmosphere to be drawn into the interior chamber via the ventilation port. The gas sensor may include an emitter and a receiver. The gas detection device can be integrated into a mobile electronic device, such as a smartphone or tablet computer.

19 Claims, 7 Drawing Sheets

(51) Int. Cl.
*G01N 21/3504* (2014.01)
*H04R 29/00* (2006.01)

(56) References Cited

U.S. PATENT DOCUMENTS

| | | | | |
|---|---|---|---|---|
| 2009/0227287 A1* | 9/2009 | Kotidis | ............... | G01J 3/02 |
| | | | | 455/556.1 |
| 2014/0134053 A1* | 5/2014 | Mayer | ............... | G01N 33/0009 |
| | | | | 422/83 |
| 2015/0201258 A1* | 7/2015 | Han | ............... | H04R 1/023 |
| | | | | 381/386 |
| 2015/0338390 A1* | 11/2015 | Anglin, Jr. | ............... | G01N 33/497 |
| | | | | 73/23.3 |
| 2016/0112781 A1* | 4/2016 | Lee | ............... | H04R 1/2803 |
| | | | | 381/332 |
| 2016/0139038 A1* | 5/2016 | Oldsen | ............... | G01J 3/42 |
| | | | | 356/454 |
| 2016/0189520 A1* | 6/2016 | Papageorge | ............... | G08B 21/12 |
| | | | | 340/632 |
| 2017/0078775 A1* | 3/2017 | McGarry | ............... | H04R 1/02 |

* cited by examiner

FIG. 5

GAS DETECTOR FOR MOBILE DEVICE INCLUDING ENCLOSURE HAVING INTERIOR CHAMBER WITH AUDIO LOUDSPEAKER, SEALED LOUDSPEAKER OPENING, VENTILATION PORT, AND GAS SENSOR

BACKGROUND

Gas detectors are used to sense the presence of one or more gases in a volume of space. Gas detectors are typically devices dedicated to the singular purpose of sensing gas. Such specialized equipment may, for example, be used to monitor an area for the presence of potentially hazardous or combustible gases, such as carbon monoxide or carbon dioxide. However, some gas detectors are not suitable for all applications. For example, gas detectors that have limited functionality and utilization may have high operating costs.

DETAILED DESCRIPTION

Gas detection devices and gas detection techniques are disclosed. In accordance with an embodiment of the present disclosure, a gas detection device includes an enclosure having an interior chamber, an audio loudspeaker in acoustic communication with the interior chamber of the enclosure, and a gas sensor configured to detect a gas within the interior chamber of the enclosure. In some cases, the device includes a ventilation port configured to permit two-way gaseous communication between the interior chamber and an atmosphere external to the enclosure, where the atmosphere includes the gas. Note that this ventilation port also can operate as a sound port for allowing output of sound from the internal loudspeaker. In some such cases, the audio loudspeaker is configured to generate a pressure within the interior chamber. The pressure causes a portion of the external atmosphere to be drawn into the interior chamber via the ventilation port. In some cases, the audio loudspeaker is configured to be driven at a frequency that is not audible by a human. In some cases, the audio loudspeaker is configured to be driven at a frequency of approximately 100 Hz or less. In some cases, the interior chamber has a volume of approximately 1,000 cubic millimeters or less. In some cases, the gas sensor includes an emitter and a receiver. In some such cases, the emitter includes a radiation source, and the receiver includes a radiation detector. In some such cases, the gas sensor includes a radiation filter disposed between the radiation source and the radiation detector. In some cases, the emitter and the receiver are disposed on or adjacent to opposing walls of the enclosure. The gas detection device can be integrated into a mobile electronic device, such as a smartphone or tablet computer. Numerous configurations and variations of such techniques will be apparent in light of this disclosure.

Many electronic devices have an integrated audio loudspeaker. In many instances, such a loudspeaker forms part of a bass reflex system. A bass reflex system is a type of vented loudspeaker enclosure that uses the sound from the rear side of the speaker diaphragm to increase the efficiency of the system at low frequencies as compared to an airtight box loudspeaker. Such enclosures include some free space around the speaker to perform effectively. The various apparatuses and methodologies disclosed herein advantageously allow a loudspeaker cavity of a bass reflex system to be utilized as a chamber for a gas sensor. Such embodiments provide significant savings in size and volume of the gas detection device, because the loudspeaker cavity can be utilized for both the speaker and the gas sensor. Moreover, and as will be further appreciated, the techniques provided in this disclosure can utilize the underutilized loudspeaker cavity space of personal computing devices (e.g., smartphones, tablets, laptops, and other devices having loudspeakers) without changing the size of those devices. Furthermore, the techniques provided in this disclosure can leverage the ability of a loudspeaker to not only provide sound but to also act as a pressure generator that can cause a portion of the external atmosphere to be drawn into the gas sensor chamber via the sound port.

Example Devices

Figure 1A:
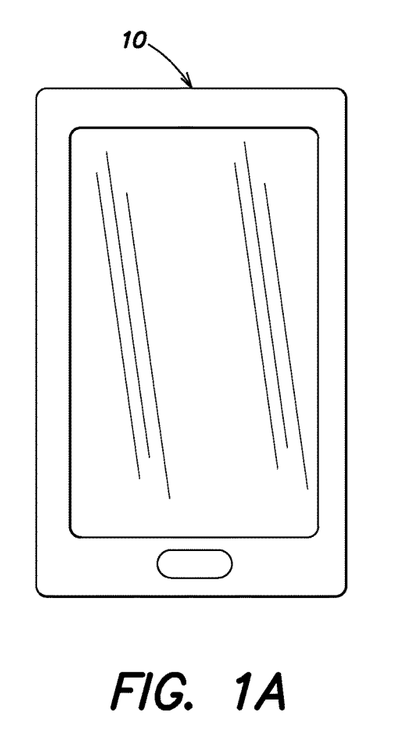
FIG. 1A shows a front view of an example gas detection device, in accordance with an embodiment of the present disclosure.
Figure 1B:
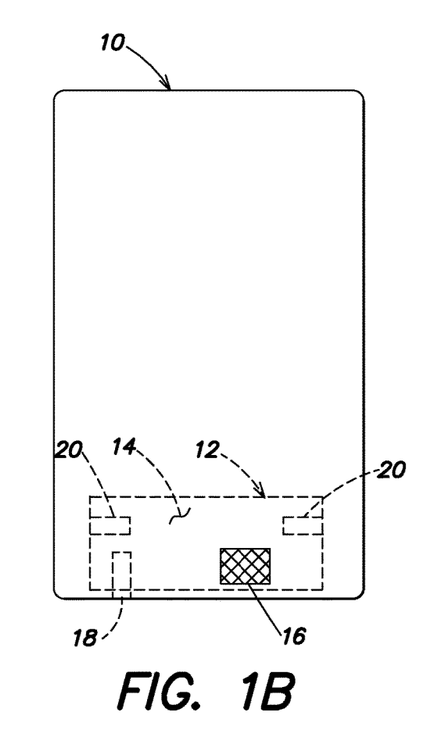
FIG. 1B shows a rear view of the example gas detection device of FIG. 1A.
Figure 1C:
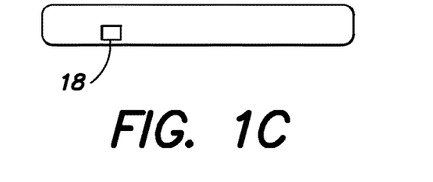
FIG. 1C shows a bottom view of the example gas detection device of FIGS. 1A and 1B.

FIGS. 1A, 1B and 1C show a front view, a rear view, and a bottom view, respectively, of an example gas detection device 10, in accordance with an embodiment of the present disclosure. However, it will be understood that the form, shape and arrangement of the device 10 and its components can vary, as will be apparent in view of this disclosure. Furthermore, although the example device 10 of FIGS. 1A-C is depicted to resemble a conventional mobile device, such as a smartphone, tablet computer, or portable music player, it will be understood that any number of different device platforms can be used without departing from the scope of the disclosure. For example, the device 10 may include a standalone loudspeaker enclosure, a laptop or desktop computer, a radio, a telephone handset, or any other device that includes an audio loudspeaker, such as will be described in further detail below. Additionally, although some embodiments of the device 10 are designed to be portable, portability of the device is not a necessary aspect of the disclosed embodiments.

The device 10 includes an enclosure 12 having an interior chamber, which is generally indicated at 14. The interior chamber is configured to at least partially contain a gas (e.g., carbon monoxide, carbon dioxide, etc.). The device 10 further includes an audio loudspeaker 16, which may be disposed adjacent to a corresponding opening (also referred to as a sound port) in the enclosure 12 so that sound from the speaker can travel out of the enclosure 12. The loudspeaker opening may be sealed to prevent the ingress or egress of gas into or out of the interior chamber 14 via the loudspeaker opening, although in some embodiments the enclosure 12 is not necessarily permanently airtight. For example, the enclosure 12 may have other permanent or temporary openings or gas permeable surfaces through which gas can enter the interior chamber 14. The diaphragm of the loudspeaker 16 is in acoustic communication with the interior chamber 14, such that pressure generated by the loudspeaker 16 travel within the interior chamber 14. The device 10 further includes a gas sensor 20, which may include one or more individual components, such as an emitter and a receiver, for detecting one or more gases. The gas sensor 20 may, for example, be disposed on, adjacent to, or within the walls of the enclosure 12 in any configuration that permits the gas sensor 20 to detect the gas within the interior chamber 14.

In some embodiments, the device 10 includes a ventilation port 18 configured to permit two-way gaseous communication between the interior chamber 14 and the atmosphere outside of the enclosure 12. For example, gas can be expelled from and drawn into the interior chamber 14 via the ventilation port 18. The ventilation port 18 may include an opening in the enclosure 12, or a tube or channel formed in the enclosure 12, that allows the ingress and egress of gas into and out of the interior chamber 14. Note that this port 18 may also be used for allow sound to be output from the device 10, such as during the playback of music or a telephone call placed on speaker phone, or an alarm in response to a gas detection. In this sense, the port 18 can be multifunctional.

Figure 2:
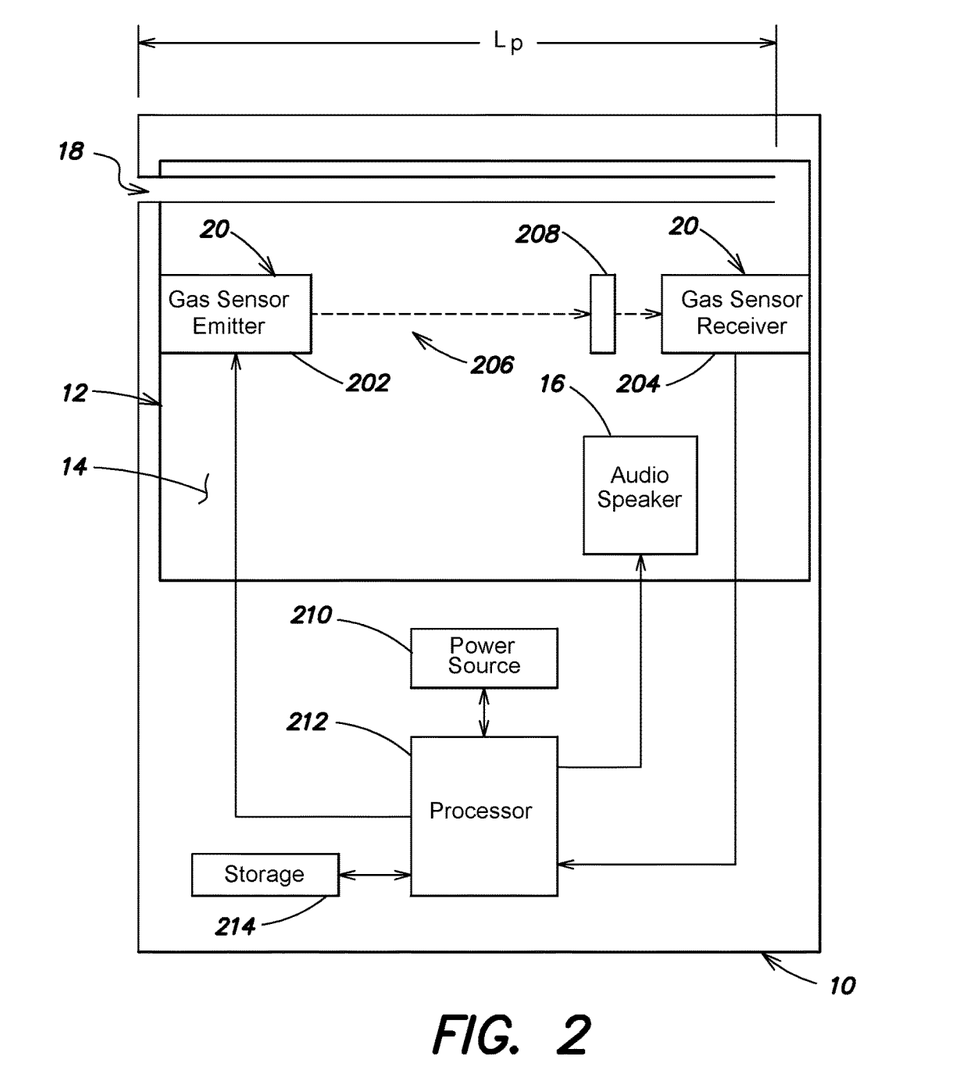
FIG. 2 shows the example gas detection device of FIGS. 1A-C in further detail, in accordance with an embodiment of the present disclosure.
Figure 3A:
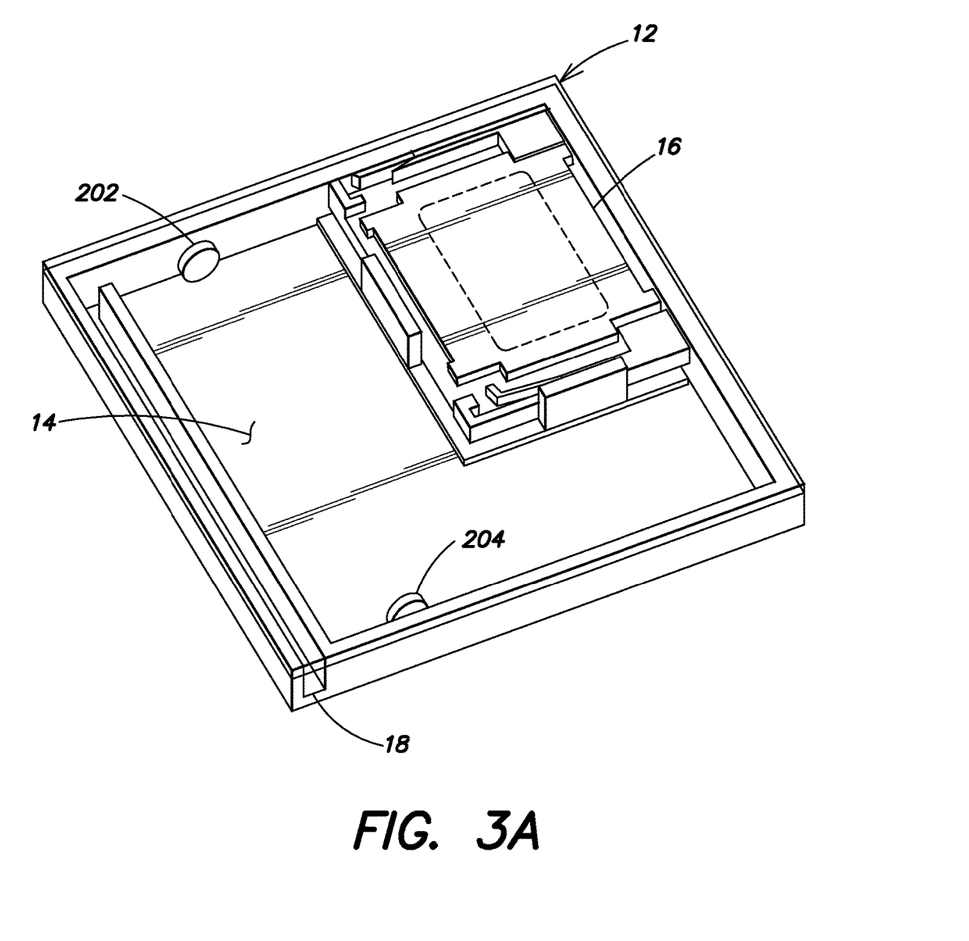
FIGS. 3A, 3B and 3C show portions of the example gas detection device of FIGS. 1A-C, in accordance with various embodiments of the present disclosure.
Figure 3B:
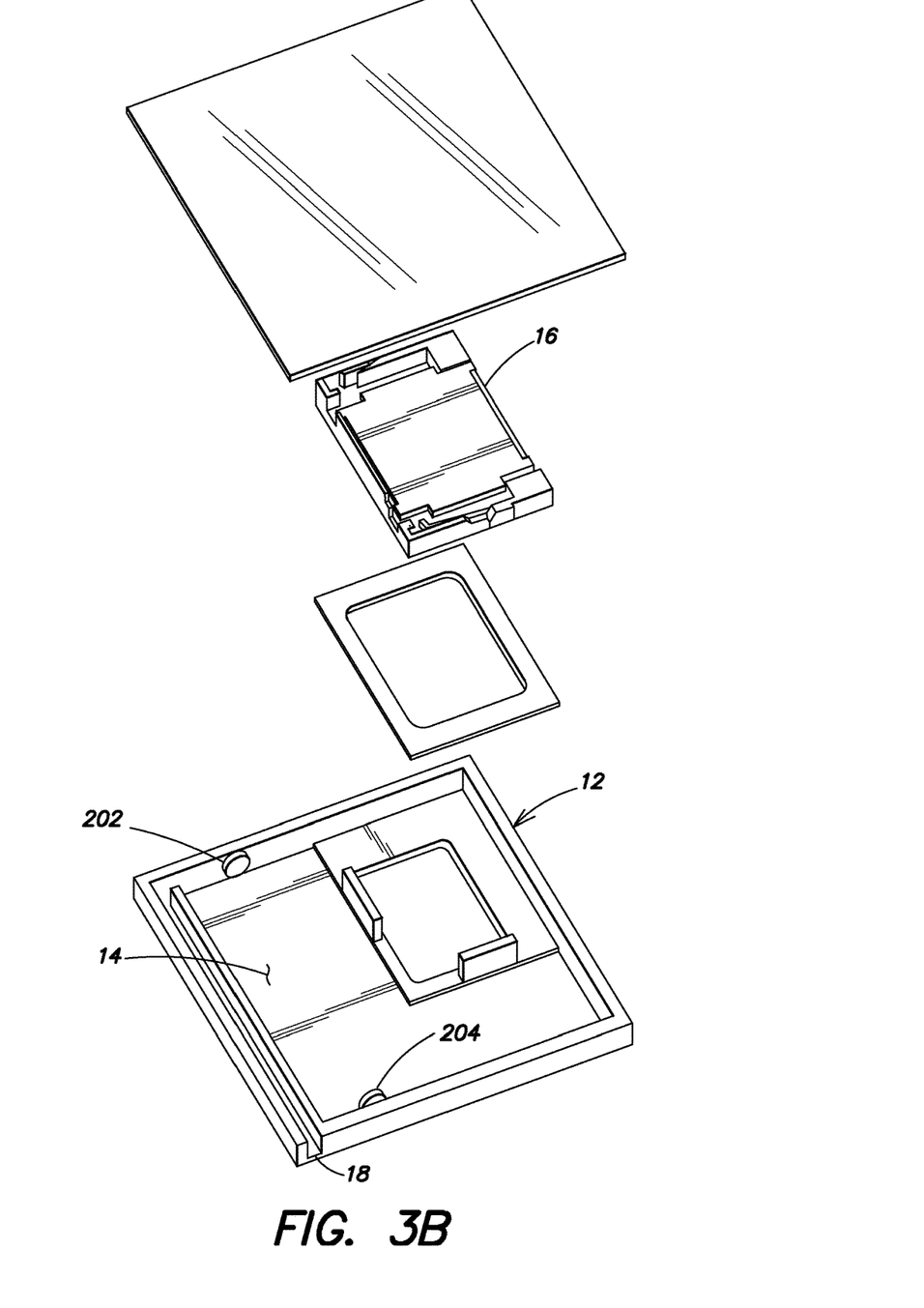
Figure 3C:
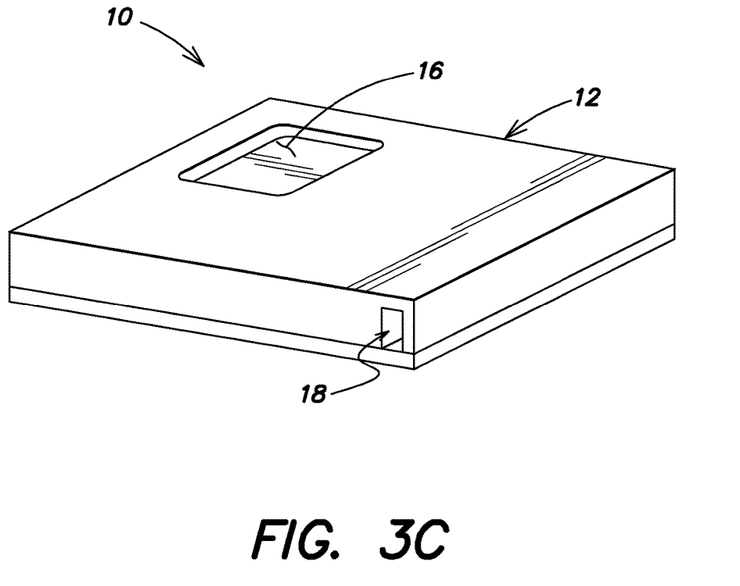
Figure 4:
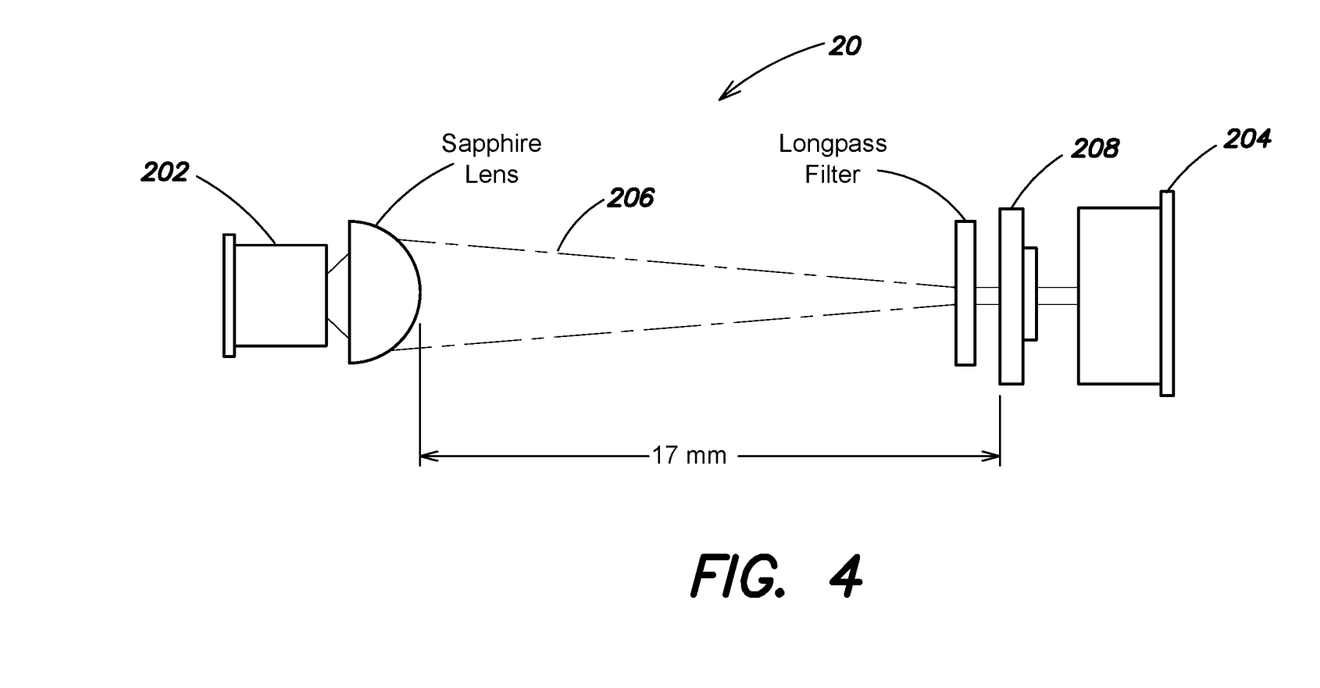
FIG. 4 shows an example gas sensor for use in the example gas detection device of FIGS. 1A-C, in accordance with an embodiment of the present disclosure.

FIG. 2 shows the example gas detection device 10 of FIGS. 1A-C in further detail, in accordance with an embodiment of the present disclosure. FIGS. 3A, 3B and 3C show portions of the example gas detection device of FIGS. 1A-C, in accordance with various embodiments of the present disclosure. In this example embodiment, the gas sensor 20 can include a spectrometry gas analyzer having an emitter 202 and a receiver 204 for emitting and receiving radiation 206, such as visible light or infrared light. An example of such a gas sensor 20 is shown in FIG. 4. The emitter 204 may include, for example, a light emitting diode (LED) or other device configured to emit broadband electromagnetic radiation such as visible light, infrared light, etc. into the interior chamber 14, which contains the gas being detected. In some embodiments, multiple emitters 202 may be used, and the emitters may emit the same or different frequencies of radiation. For example, a first emitter may emit visible light and a second emitter may emit infrared light. The gas sensor 20 may have, for example, a wavelength range of between approximately 3000 and 3500 nanometers, a spectral resolution of between approximately 50 and 60 nanometers, an optical path length of approximately 17 millimeters, a size of approximately 77×38×25 millimeters, or any combination of these characteristics. However, it will be understood that other suitable gas sensors and analyzers are within the scope of this disclosure. For instance, some embodiments of the device 10 as variously described in this disclosure are agnostic to the type of gas sensor 20, such that any suitable gas sensor may be substituted for, or supplemented by, another type of gas sensor. Some example sensor types and structures that can be used in an embodiment of the present disclosure include, for instance, infrared point sensors, infrared imaging sensors (active and passive), holographic sensors, ultrasonic sensors (which use acoustic sensors to compare normal background noise to escalated noise attributable to a gas leak), electrochemical gas sensors (which typically have an electrode and porous membrane configuration), semiconductor sensors (which use a semiconductor material such as tin dioxide to detect gas concentration based on a change in resistance or other measurable electrical property of the semiconductor material when exposed to the target gas), carbon monoxide and carbon dioxide sensors, breathalyzers (for detecting alcohol), volatile organic compound or so-called VOC sensors (e.g., hydrocarbon sensors), and water vapor sensors. Note that some example embodiments may utilize a sensor that can measure concentration of a target gas while other example embodiments may employ sensors that cannot measure concentration of a target gas but can still indicate the presence of a target gas. Numerous other means for detecting a gas within the interior chamber 14 will be apparent in light of this disclosure. In any such cases, the loudspeaker 16 can be used to entrain or otherwise draw ambient air into the sensor chamber 14 so that the sensor 20 can then operate as it normally does, and data output by the gas sensor 20 can then be used for various purposes (e.g., cause an alarm, generate a report, notify maintenance personnel or the authorities, generate a pop-up window to the user, forward sensed data to a cloud-based repository, to name a few possible actions that can be taken in response to a gas detection signal being generated). Further note that the loudspeaker 16 may also be used for generate sound to be output from the device 10, such as during the playback of music or a telephone call placed on speaker phone. Likewise, the loudspeaker 16 may also be used to sound an alarm if a gas is detected. In this sense, the loudspeaker 16 can be multifunctional in that it is configured to both input ambient air into the chamber 14 and output sound.

As shown in FIG. 2, the emitter 202 and the receiver 204 may, for example, be mounted on or within opposing walls of the enclosure 12 such that most or substantially all of the volume of the interior chamber 14 lies between the emitter 202 and the receiver 204. In another example, the emitter 202 and the receiver 204 may be mounted outside of the enclosure 12 such that the radiation emitted by the emitter 202 passes through a transparent portion of the enclosure 12 wall (e.g., a glass or plastic window) and into the interior chamber 14. The device 10 can include a power source 210, such as a battery, at least one computer processor 212, and at least one storage 214. The power source 210 can be configured to provide energy to any component of the device 10, including the loudspeaker 16, the gas sensor 20, and the processor 212.

Referring still to FIG. 2, the processor 212 can be any suitable processor, and may include one or more coprocessors or controllers to assist in control and processing operations associated with the device 10. The storage 214 can be implemented using any suitable type of digital storage, such as one or more of a disk drive, a universal serial bus (USB) drive, flash memory and/or random access memory (RAM). The processor 212 is configured to execute an operating system, which may include any suitable operating system, such as Linux, Google Android (Google Inc., Mountain View, Calif.), Microsoft Phone (Microsoft Corp., Redmond, Wash.), or Apple iOS (Apple Inc., Cupertino, Calif.). As will be appreciated in light of this disclosure, the techniques provided herein can be implemented without regard to the particular operating system provided in conjunction with processor 212, and therefore may also be implemented using any suitable existing or subsequently-developed platform. The power source 210 can include a battery or other component for storing an electrical charge, which powers the various components of the device 10, including the emitter 202, the receiver 204, the loudspeaker 16, and the processor 212. In some embodiments, the device 10 includes charging circuitry operatively coupled to the power source 210 for charging the power source 210. Any suitable power source technology can be used, including renewable power sources such as photovoltaic cells or power scavenging circuitry, or a combination of such sources such as a battery supplemented with photovoltaic cells. Numerous power schemes will be appreciated.

The various embodiments disclosed herein can be implemented in various forms of hardware, software, firmware, and/or special purpose processors. For example in one embodiment a non-transitory computer readable medium has instructions encoded thereon that, when executed by one or more processors, cause one or more of the methodologies disclosed herein to be implemented. The instructions can be encoded using a suitable programming language, such as C, C++, object oriented C, JavaScript, Visual Basic .NET, Beginner's All-Purpose Symbolic Instruction Code (BASIC), or alternatively, using custom or proprietary instruction sets. The instructions can be provided in the form of one or more computer software applications and/or applets that are tangibly embodied on a memory device, and that can be executed by a computer having any suitable architecture. In one embodiment, the system can be implemented, for example, using JavaScript or another suitable technology. The computer software methodologies disclosed herein may include any number of different modules, sub-modules, or other components of distinct functionality, and can provide information to, or receive information from, still other components. These modules can be used, for example, to communicate with input and/or output devices such as a display screen, a touch sensitive surface, a printer, and/or any other suitable device. Other componentry and functionality not reflected in the illustrations will be apparent in light of this disclosure, and it will be appreciated that other embodiments are not limited to any particular hardware or software configuration. Thus in other embodiments the device 10 may have additional, fewer, or alternative subcomponents as compared to those included in the example embodiment of FIG. 2.

The aforementioned non-transitory computer readable medium may be any suitable medium for storing digital information, such as a hard drive, a server, a flash memory, and/or random access memory (RAM). In alternative embodiments, the components and/or modules disclosed herein can be implemented with hardware, including gate level logic such as a field-programmable gate array (FPGA), or alternatively, a purpose-built semiconductor such as an application-specific integrated circuit (ASIC). Still other embodiments may be implemented with a microcontroller having a number of input/output ports for receiving and outputting data, and a number of embedded routines for carrying out the various functionalities disclosed herein. It will be apparent that any suitable combination of hardware, software, and firmware can be used, and that other embodiments are not limited to any particular system architecture.

Spectrometry gas analyzers, such as described with respect to FIGS. 2, 3A, 3B and 3C, operate under the principle that different gases have unique resonant frequencies at which the gases absorb the electromagnetic radiation. Since the gas being tested absorbs radiation at the frequency being measured, it is possible to measure the concentration of the gas in the interior chamber 14 by the amplitude of the detected signals. The accuracy of the measurement may improve as a function of the distance the electromagnetic wave travels in the medium, and therefore in some embodiments the distance between the emitter 202 and the receiver 204 is as large as possible. In some cases, the gas sensor 20 includes a filter 208, such as an interferometer, which can be used to filter out certain frequencies of the radiation 206 before the radiation reaches the receiver 204.

Referring to FIGS. 2, 3A, 3B and 3C, in various embodiments, the enclosure 12 can include a bass reflex system (also referred to as a ported, vented box or a reflex port), which is a type of loudspeaker enclosure that uses the pressure from the rear side of the loudspeaker 16 diaphragm to increase the efficiency of the system at low frequencies, as compared to a closed box loudspeaker. Bass reflex systems can be used in mobile devices, which have very small speakers, although the acoustical benefit is small. However, according to various embodiments, a bass reflex system can be used for gas detection and, in some cases, for ventilation of the gas into and out of the enclosure 12. In some embodiments, the loudspeaker 16 can be driven at frequencies that are below the cut-off frequency of that particular speaker, and thus not producing any audible noise. The pressure created at these frequencies generates a flow of gas that has the effect of exchanging at least some of the gas inside the enclosure 12 with the external atmosphere. Unlike closed box loudspeakers, which are substantially airtight, the bass reflex system of some embodiments includes the ventilation port 18, which may variously include a pipe or duct having a circular or rectangular cross section.

The air mass within the ventilation port 18 resonates with the so-called springiness of the gas inside the enclosure 12, similar to the manner in which air in a bottle resonates when a current of air is directed across the opening of the bottle. The frequency at which the bass reflex system resonates, known as the Helmholtz resonance, depends upon the effective length and cross sectional area of the ventilation port 18, the volume of the interior chamber 14, and the speed of sound in air. When the springiness resonance is so chosen as to lie lower in frequency than the natural resonance frequency of the bass driver (e.g., the loudspeaker 16), the back wave of the bass driver sound emission is inverted in polarity for the frequency range between the two resonances. Since the back wave is in opposite polarity with the front wave, the polarity inversion brings the two emissions in phase, and therefore they reinforce each other. This has the beneficial purpose of producing higher output, as compared to a closed box system.

The dimensions of the ventilation port 18 can be calculated using known electromechanical parameters (e.g., Thiele/Small parameters), which define the low frequency performance of a particular loudspeaker driver, as a function of the volume of the enclosure 12. The electromechanical parameters may, for instance, be published by driver manufacturers in specification sheets so that designers have a guide for selecting loudspeaker drivers. Using these parameters, the dimensions of the ventilation port 18 (e.g., the cross sectional area and length) can be calculated as follows.

In one example embodiment, with reference to Thiele/Small parameters $Q_{ES}$ and $Q_{MS}$, the total quality factor can be calculated using the following equation:

$$Q_{TS} = \frac{Q_{ES}Q_{MS}}{Q_{ES} + Q_{MS}}$$

Using electromechanical parameters and other information, the dimensions of the ventilation port 18 can be calculated. For example, the gas sensor 20 may include a Fabry-Perot gas sensor having approximately a 17 millimeter optical path length, such as shown in FIG. 4. In this example, the length $L_p$ of the optical path may, for example, be at least 17 millimeters. The cross sectional area of the ventilation port 18 affects the port length. The cross sectional area of the ventilation port 18 may be defined such that the size is feasible for use with certain mobile devices. For example, in some embodiments the ventilation port 18 may have a cross-sectional area of approximately 1 by 3 millimeters, and a length of approximately 30 millimeters, which is suitable for use in many portable electronic devices.

For a given application, the Helmholtz tuning ratio may, for example, be obtained from the vented box alignment chart utilizing a known QTS factor.

The length $L_p$ of the port can be calculated with following formula:

$$L_p = \left(\frac{c}{2\pi f_b}\right)^2 \frac{S_P}{V_{AB}} - 1.463\sqrt{\frac{S_P}{\pi}}$$

Where $f_b$ is the Helmholtz tuning frequency and $S_P$ is the cross-sectional area of the ventilation port 18. In one example, $S_P=3$ mm$^2$ defines the port length $L_p$ to be 30 mm, which is a suitable dimension for optical gas sensor integration. The volume $V_{AB}$ of the enclosure 12 may, in some cases, be constrained by the size of the device 10, such as 1,000 cubic millimeters or less, or 2 cubic centimeters or less. For example, the volume of the enclosure 12 may be approximately 30 by 30 millimeters, or 27 by 29 millimeters, etc. It will be understood that, according to various embodiments, the shape of the enclosure 12 can vary. For the example dimensions described above, an optical gas sensor 20 can be integrated into the device 10 such as shown in FIGS. 3A, 3B and 3C.

Methodology

Figure 5:
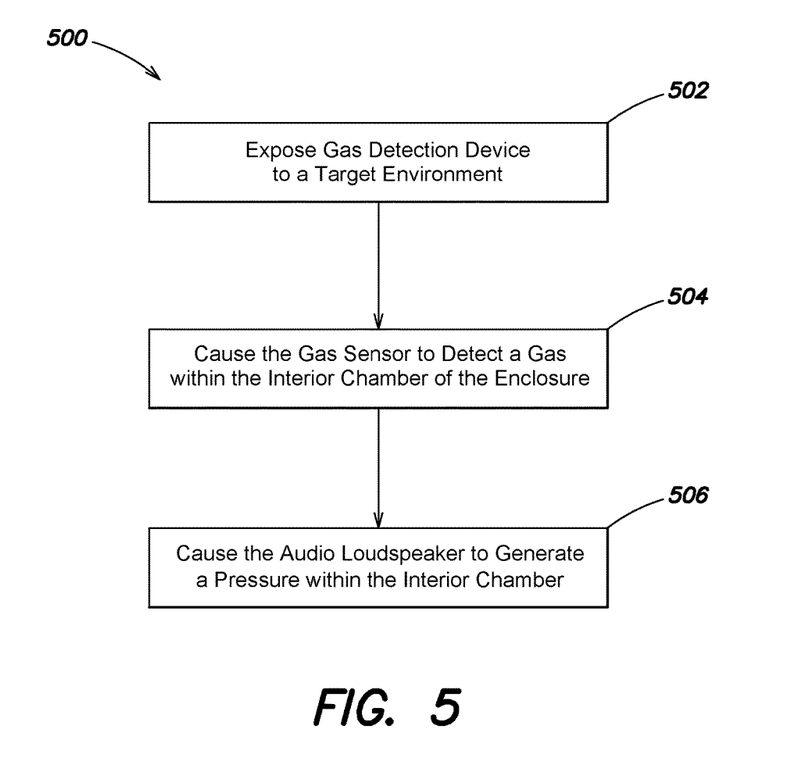
FIG. 5 is a flowchart illustrating an example method for detecting a gas using the example gas detection device of FIGS. 1A-C, in accordance with an embodiment of the present disclosure.

FIG. 5 is a flowchart illustrating an example method 500 for detecting a gas using a gas detection device, such as the gas detection device 10 of FIG. 1 or 2, in accordance with an embodiment of the present disclosure. As can be seen, example method 500 includes a number of acts, the sequence of which may vary from one embodiment to another. However, when considered in the aggregate, act form a gesture detection process in accordance with certain of the embodiments disclosed herein. These embodiments can be implemented, for example using any of the architectures illustrated in FIGS. 1 and 2, as described above. However other architectures can be used in other embodiments, as will be apparent in light of this disclosure. To this end, the correlation of the various functions shown in FIG. 5 to the specific components illustrated in FIGS. 1 and 2 is not intended to imply any structural and/or use limitations. Rather other embodiments may include, for example, varying degrees of integration wherein multiple functionalities are effectively performed by one system. For example, in an alternative embodiment some or all of the functions of method 500 can be performed by a remote device. Numerous variations and alternative configurations will be apparent in light of this disclosure.

The method 500 includes a process for detecting a gas using a gas detection device. The gas detection device includes an enclosure having an interior chamber, an audio loudspeaker in acoustic communication with the interior chamber of the enclosure, and a gas sensor configured to detect a gas within the interior chamber of the enclosure. The method 500 includes exposing a gas detection device to a target environment 502. The gas detection device may include an enclosure having an interior chamber, an audio loudspeaker in acoustic communication with the interior chamber of the enclosure, and a gas sensor configured to detect a gas within the interior chamber of the enclosure. The method 500 further includes causing the gas sensor to detect a gas within the interior chamber of the enclosure 504. In some cases, the gas detection device includes a ventilation port configured to permit two-way gaseous communication between the interior chamber and an atmosphere external to the enclosure, where the atmosphere comprises the gas. In such cases, the method 500 includes causing the audio loudspeaker to generate a pressure within the interior chamber 506. The pressure causes a portion of the atmosphere to be drawn into the interior chamber via the ventilation port, such that the gas in the atmosphere is present in the interior chamber for detection by the gas sensor. In some cases, causing the audio loudspeaker to generate a pressure within the interior chamber 504 includes driving the audio loudspeaker at a frequency below the lower cut-off frequency of the speaker, for instance, where the loudspeaker does not produce any audible noise. In some cases, the interior chamber has a volume of approximately 1000 cubic millimeters or less. In some cases, the gas sensor comprises an emitter and a receiver. In some cases, the emitter includes a radiation source, and wherein the receiver comprises a radiation detector. In some such cases, device includes a radiation filter disposed between the radiation source and the radiation detector. In some cases, the emitter and the receiver are disposed on or adjacent to opposing walls of the enclosure. In some cases, a mobile electronic device, such as a smartphone, table computer, or laptop computer, can be configured to perform any or all of the method 500.

Various embodiments may be implemented using hardware elements, software elements, or a combination of both. Examples of hardware elements may include processors, microprocessors, circuits, circuit elements (for example, transistors, resistors, capacitors, inductors, and so forth), integrated circuits, ASICs, programmable logic devices, digital signal processors, FPGAs, logic gates, registers, semiconductor devices, chips, microchips, chipsets, and so forth. Examples of software may include software components, programs, applications, computer programs, application programs, system programs, machine programs, operating system software, middleware, firmware, software modules, routines, subroutines, functions, methods, procedures, software interfaces, application program interfaces, instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power level, heat tolerances, processing cycle budget, input data rates, output data rates, memory resources, data bus speeds, and other design or performance constraints.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled", however, may also mean that two or more elements are not in direct contact with each other, but yet still cooperate or interact with each other.

Some embodiments may be implemented, for example, using a machine readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, process, or the like, and may be implemented using any suitable combination of hardware and/or software. The machine readable medium or article may include, for example, any suitable type of memory unit, memory device, memory article, memory medium, storage device, storage article, storage medium, and/or storage unit, such as memory, removable or non-removable media, erasable or non-erasable media, writeable or rewriteable media, digital or analog media, hard disk, floppy disk, compact disk read only memory (CD-ROM), compact disk recordable (CD-R) memory, compact disk rewriteable (CR-RW) memory, optical disk, magnetic media, magneto-optical media, removable memory cards or disks, various types of digital versatile disk (DVD), a tape, a cassette, or the like. The instructions may include any suitable type of code, such as source code, compiled code, interpreted code, executable code, static code, dynamic code, encrypted code, and the like, implemented using any suitable high level, low level, object oriented, visual, compiled, and/or interpreted programming language.

Unless specifically stated otherwise, it may be appreciated that terms such as "processing", "computing", "calculating", "determining", or the like refer to the action and/or process of a computer or computing system, or similar electronic computing device, that manipulates and/or transforms data represented as physical quantities (for example, electronic) within the registers and/or memory units of the computer system into other data similarly represented as physical quantities within the registers, memory units, or other such information storage transmission or displays of the computer system. The embodiments are not limited in this context.

Numerous specific details have been set forth herein to provide a thorough understanding of the embodiments. It will be understood by an ordinarily-skilled artisan, however, that the embodiments may be practiced without these specific details. In other instances, well known operations, components and circuits have not been described in detail so as not to obscure the embodiments. It can be appreciated that the specific structural and functional details disclosed herein may be representative and do not necessarily limit the scope of the embodiments. In addition, although the subject matter has been described in language specific to structural features and/or methodological acts, it is to be understood that the subject matter defined in the appended claims is not necessarily limited to the specific features or acts described herein. Rather, the specific features and acts described herein are disclosed as example forms of implementing the claims.

Further Example Embodiments

The following examples pertain to further embodiments, from which numerous permutations and configurations will be apparent.

Example 1 is a gas detection device. The device includes an enclosure having an interior chamber, an audio loudspeaker in acoustic communication with the interior chamber of the enclosure, and a gas sensor configured to detect a gas within the interior chamber of the enclosure.

Example 2 includes the subject matter of Example 1, further including a ventilation port configured to permit two-way gaseous communication between the interior chamber and an atmosphere external to the enclosure, where the atmosphere comprises the gas.

Example 3 includes the subject matter of Example 2, where the audio loudspeaker is configured to generate a pressure within the interior chamber, and where the pressure causes a portion of the atmosphere to be drawn into the interior chamber via the ventilation port.

Example 4 includes the subject matter of any of Examples 1-3, where the audio loudspeaker is configured to be driven at a frequency where the audio loudspeaker does not produce any noise audible to a human.

Example 5 includes the subject matter of any of Examples 1-4, where the audio loudspeaker is configured to be driven to output sound including music, audio portion of a video, human conversation being carried out using the device, a computer generated voice, or any combination of these.

Example 6 includes the subject matter of any of Examples 1-5, where the interior chamber has a volume of approximately 1000 cubic millimeters or less.

Example 7 includes the subject matter of any of Examples 1-6, where the gas sensor includes an emitter and a receiver.

Example 8 includes the subject matter of Example 7, where the emitter includes a radiation source, and where the receiver includes a radiation detector.

Example 9 includes the subject matter of Example 8, further including a radiation filter disposed between the radiation source and the radiation detector.

Example 10 includes the subject matter of any of Examples 7-9, where the emitter and the receiver are disposed on or adjacent to opposing walls of the enclosure.

Example 11 includes the subject matter of any of Examples 1-10, where the gas sensor includes a semiconductor material that changes in its electrical properties when exposed to a target gas.

Example 12 includes the subject matter of any of Examples 1-10, where the gas sensor includes an electrode and porous membrane configuration.

Example 13 is mobile electronic device including the subject matter of any of Examples 1-12.

Example 14 includes the subject matter of Example 13, where the mobile electronic device is one of a smartphone, a tablet computer, and a laptop computer.

Example 15 is a method for detecting a gas. The method includes exposing a gas detection device to a target environment. The gas detection device includes an enclosure having an interior chamber, an audio loudspeaker in acoustic communication with the interior chamber of the enclosure, and a gas sensor configured to detect a gas within the interior chamber of the enclosure. The method further includes causing the gas sensor to detect a gas within the interior chamber of the enclosure.

Example 16 includes the subject matter of Example 15, where the gas detection device further includes a ventilation port configured to permit two-way gaseous communication between the interior chamber and an atmosphere external to the enclosure, and where the atmosphere comprises the gas. The method further includes causing the audio loudspeaker to generate a pressure within the interior chamber, the pressure causing a portion of the atmosphere to be drawn into the interior chamber via the ventilation port.

Example 17 includes the subject matter of any of Examples 15-16, where the method further includes driving the audio loudspeaker at a frequency where the audio loudspeaker does not produce any noise audible to a human.

Example 18 includes the subject matter of any of Examples 15-17, where the interior chamber has a volume of approximately 1000 cubic millimeters or less.

Example 19 includes the subject matter of any of Examples 15-18, where the gas sensor includes an emitter and a receiver.

Example 20 includes the subject matter of Example 19, where the emitter includes a radiation source, and where the receiver includes a radiation detector.

Example 21 includes the subject matter of Example 20, where the device further includes a radiation filter disposed between the radiation source and the radiation detector.

Example 22 includes the subject matter of any of Examples 19-21, where the emitter and the receiver are disposed on or adjacent to opposing walls of the enclosure.

Example 23 includes the subject matter of any of Examples 15-22, where the gas sensor includes a semiconductor material that changes in its electrical properties when exposed to a target gas.

Example 24 includes the subject matter of any of Examples 15-22, where the gas sensor includes an electrode and porous membrane configuration.

Example 25 is a mobile electronic device configured to perform the method of any of Examples 15-24.

Example 26 includes the subject matter of Example 25, where the mobile electronic device is one of a smartphone, a tablet computer, and a laptop computer.

Example 27 is a gas detection device. The device includes an enclosure having an interior chamber, an audio loudspeaker in acoustic communication with the interior chamber of the enclosure, and means for detecting a gas within the interior chamber of the enclosure.

Example 28 includes the subject matter of Example 27, further including a ventilation port configured to permit two-way gaseous communication between the interior chamber and an atmosphere external to the enclosure, where the atmosphere comprises the gas.

Example 29 includes the subject matter of Example 28, where the audio loudspeaker is configured to generate a pressure within the interior chamber, the pressure causing a portion of the atmosphere to be drawn into the interior chamber via the ventilation port.

Example 30 includes the subject matter of any of Examples 27-29, where the audio loudspeaker is configured to be driven at a frequency where the audio loudspeaker does not produce any noise audible to a human.

Example 31 includes the subject matter of any of Examples 27-30, where the audio loudspeaker is configured to be driven to output audible sound including at least one of music, audio portion of a video, human conversation being carried out using the device, and a computer generated voice.

Example 32 includes the subject matter of any of Examples 27-31, where the interior chamber has a volume of approximately 1000 cubic millimeters or less.

Example 33 includes the subject matter of any of Examples 27-32, where the means for detecting the gas includes an emitter and a receiver.

Example 34 includes the subject matter of Example 33, where the emitter includes a radiation source, and where the receiver includes a radiation detector.

Example 35 includes the subject matter of Example 34, further including a radiation filter disposed between the radiation source and the radiation detector.

Example 36 includes the subject matter of any of Examples 33-35, where the emitter and the receiver are disposed on or adjacent to opposing walls of the enclosure.

Example 37 includes the subject matter of any of Examples 27-32, where the means for detecting the gas includes an electrode and a porous membrane.

Example 38 includes the subject matter of any of Examples 27-32, where the means for detecting the gas includes a semiconductor material that changes in its electrical properties when exposed to a target gas.

Example 39 is a mobile electronic device including the subject matter of any of Examples 27-38.

The foregoing description of example embodiments is presented for the purposes of illustration and description. It is not intended to be exhaustive or to limit this disclosure to the precise forms described. Many modifications and variations are possible in light of this disclosure. It is intended that the scope of the present disclosure be limited not be this detailed description, but rather by the claims appended hereto. Future filed applications claiming priority to this application may claim the disclosed subject matter in a different manner, and may generally include any set of one or more elements as variously disclosed or otherwise demonstrated herein.

What is claimed is:

1. A gas detection device comprising:
   an enclosure having an interior chamber;
   an audio loudspeaker in acoustic communication with the interior chamber of the enclosure;
   a gas sensor configured to detect a gas within the interior chamber of the enclosure;
   a ventilation port comprising a channel within the enclosure, the channel configured to permit two-way gaseous communication between the interior chamber and an atmosphere external to the enclosure, wherein the atmosphere comprises the gas; and
   a loudspeaker opening in the enclosure, the loudspeaker opening being sealed to prevent ingress or egress of the gas into or out of the interior chamber via the loudspeaker opening,
   wherein the channel has a length and a cross-sectional area, the length defined as a function of the cross-sectional area of the channel, a volume of the interior chamber which is 1000 cubic millimeters or less, and a Helmholtz resonance of the enclosure below a cut-off frequency at which the audio loudspeaker does not produce any audible noise.

2. The device of claim 1, wherein the audio loudspeaker is configured to generate a pressure within the interior chamber, the pressure causing a portion of the atmosphere to be drawn into the interior chamber via the ventilation port.

3. The device of claim 1, wherein the audio loudspeaker is configured to be driven below a cut-off frequency at which the audio loudspeaker does not produce any noise.

4. The device of claim 1, wherein the audio loudspeaker is configured to be driven to output sound including at least one of music, audio portion of a video, human conversation being carried out using the device, and a computer-generated voice.

5. The device of claim 1, wherein the gas sensor comprises an emitter and a receiver.

6. The device of claim 5, wherein the emitter comprises a radiation source, and wherein the receiver comprises a radiation detector.

7. The device of claim 6, further comprising a radiation filter disposed between the radiation source and the radiation detector.

8. The device of claim 5, wherein the emitter and the receiver are disposed on or adjacent to opposing walls of the enclosure.

9. The device of claim 1, wherein the gas sensor comprises a semiconductor material that changes in its electrical properties when exposed to a target gas.

10. The device of claim 1, wherein the gas sensor comprises an electrode and porous membrane configuration.

11. A mobile electronic device comprising the device of claim 1, wherein the mobile electronic device is one of a smartphone, a tablet computer, and a laptop computer.

12. The device of claim 1, wherein the channel has a length and a cross-sectional area, the length defined as:

$$L_p = \left(\frac{c}{2\pi f_b}\right)^2 \frac{S_P}{V_{AB}} - 1.463\sqrt{\frac{S_P}{\pi}}$$

where $L_p$ is the length of the channel, $f_b$ is the Helmholtz tuning frequency, $V_{AB}$ is a volume of the interior chamber, c is a constant value, and $S_P$ is the cross-sectional area of the channel.

13. A method for detecting a gas, the method comprising:
exposing a gas detection device to a target environment, the gas detection device comprising an enclosure having an interior chamber, an audio loudspeaker in acoustic communication with the interior chamber of the enclosure, a gas sensor configured to detect a gas within the interior chamber of the enclosure, a ventilation port comprising a channel within the enclosure, the channel configured to permit two-way gaseous communication between the interior chamber and an atmosphere external to the enclosure, wherein the atmosphere comprises the gas, and a loudspeaker opening in the enclosure, the loudspeaker opening being sealed to prevent ingress or egress of the gas into or out of the interior chamber via the loudspeaker opening, wherein the channel has a length and a cross-sectional area, the length defined as a function of the cross-sectional area of the channel, a volume of the interior chamber which is 1000 cubic millimeters or less, and a Helmholtz resonance of the enclosure below a cut-off frequency at which the audio loudspeaker does not produce any audible noise; and
causing the gas sensor to detect a gas within the interior chamber of the enclosure.

14. The method of claim 12, wherein the method further comprises causing the audio loudspeaker to generate a pressure within the interior chamber, the pressure causing a portion of the atmosphere to be drawn into the interior chamber via the ventilation port.

15. The method of claim 12, further comprising driving the audio loudspeaker below a cut-off frequency at which the audio loudspeaker does not produce any noise.

16. The method of claim 12, wherein the interior chamber has a volume of approximately 1000 cubic millimeters or less.

17. The method of claim 12, wherein the gas sensor comprises an emitter and a receiver.

18. The method of claim 17, wherein the emitter comprises a radiation source, and wherein the receiver comprises a radiation detector.

19. A gas detection device comprising:
an enclosure having an interior chamber;
an audio loudspeaker in acoustic communication with the interior chamber of the enclosure;
means for detecting a gas within the interior chamber of the enclosure;
a ventilation port comprising a channel within the enclosure, the channel configured to permit two-way gaseous communication between the interior chamber and an atmosphere external to the enclosure, wherein the atmosphere comprises the gas; and
a loudspeaker opening in the enclosure, the loudspeaker opening being sealed to prevent ingress or egress of the gas into or out of the interior chamber via the loudspeaker opening,
wherein the channel has a length and a cross-sectional area, the length defined as a function of the cross-sectional area of the channel, a volume of the interior chamber which is 1000 cubic millimeters or less, and a Helmholtz resonance of the enclosure below a cut-off frequency at which the audio loudspeaker does not produce any audible noise.

* * * * *